US006942993B2

(12) United States Patent
Qiu

(10) Patent No.: US 6,942,993 B2
(45) Date of Patent: Sep. 13, 2005

(54) ENGINEERED ANTIBIOTIC PEPTIDES AND THE PREPARATION THEREOF

(75) Inventor: Xiaoqing Qiu, Chengdu (CN)

(73) Assignee: Sichuan NTC Holdings Limited, Chengdu (CN)

( * ) Notice: Subject to any disclaimer, the term of this patent is extended or adjusted under 35 U.S.C. 154(b) by 521 days.

(21) Appl. No.: 10/241,564

(22) Filed: Sep. 9, 2002

(65) Prior Publication Data

US 2003/0078207 A1 Apr. 24, 2003

(30) Foreign Application Priority Data

Sep. 11, 2001 (CN) .......................................... 01128836 A

(51) Int. Cl.[7] .......................... C12P 21/02; A61K 38/16; C07K 14/195
(52) U.S. Cl. .......................... 435/69.1; 514/12; 530/350
(58) Field of Search .......................... 435/69.1; 514/12; 530/350

(56) References Cited

U.S. PATENT DOCUMENTS

| | | | |
|---|---|---|---|
| 5,777,078 | A | 7/1998 | Bayley et al. |
| 5,817,771 | A | 10/1998 | Bayley et al. |
| 5,824,776 | A | 10/1998 | Bayley et al. |
| 6,100,042 | A * | 8/2000 | Fowlkes et al. ............. 435/7.1 |
| 6,447,786 | B1 | 9/2002 | Novick et al. |
| 2003/0078378 | A1 | 4/2003 | Novick et al. |

FOREIGN PATENT DOCUMENTS

| | | |
|---|---|---|
| CN | 1341604 | 3/2002 |
| CN | 1396178 | 2/2003 |
| WO | WO 94/25616 | 11/1994 |
| WO | WO 96/20688 | 7/1996 |
| WO | WO 03/106483 A1 | 12/2003 |
| WO | WO 04/082701 A1 | 9/2004 |
| WO | WO 04/083437 A1 | 9/2004 |
| WO | WO 04/083438 A1 | 9/2004 |

OTHER PUBLICATIONS

Genbank Accession No. M13819, Plasmid Colla.
Ji et al., "Cell Density Control of Staphylococcal Virulence Mediated by an Octapeptide Pheromone", *Proc. Natl. Acad. Sci. USA*, 92:12055–12059 (1985).
Mankovich et al., "DNA and Amino Acid Sequence Analysis of Structural and Immunity Genes of Colicin Ia and Ib", 168(1):228–236 (1986).
Mayville et al., "Structure–activity analysis of synthetic autoinducing thiolactone peptides from *Staphylococcus aerus* responsible for virulence", *Proc. Natl. Acad. Sci. USA*, 96:1218–1223 (1999).
Schein et al., "Colicin K acts by forming voltage–dependent channels in phospholipid bilayer membranes", *Nature*, 276:159–163 (1978).
Slatin et al., "Identification of a translocated protein segment in a voltage–dependent channel", *Nature*, 371:158–161 (1994).
Qiu et al., "Major Transmembrane Movement Associated with Colicin Ia Channel Gating", *J. Gen. Physiol.*, 107:313–328 (1996).
Qiu et al., "Site–specific Biotinylation of Colicin Ia", *Journal of Biological Chemistry*, 269(10):7483–7488 (1994).
Genbank Accession No. U85097.
Dunny et al., "Cell–cell communication in gram–positive bacteria", *Annu. Rev. Microbiol.*, 51:527–564 (1997).
Kienker et al., "Transmembrane insertion of the colicin Ia hydrophobic hairpin", *J. Memb. Biol.*, 157:27–37 (1997).
Qiu et al., "Inherent TEA–binding ability of shIR K[+] channel induces blockade in a bacteria protein toxin", Society for Neuroscience 31st Ann. Meeting. San Diego, CA. Nov. 10–15 (2001). Program No. 812.24.
Huster, D., et al. "Solid–state NMR investigation of the dynamics of the soluble and membrane–bound colicin Ia channel–forming domain." *Biochemistry*. Jun. 26, 2001; 40(25):7662–74.
Huster, D., et al. "Conformational changes of colicin Ia channel–forming domain upon membrane binding: a solid–state NMR study." *Biochim Biophys Acta*. Apr. 12, 2002; 1561(2):159–70.
Kienker, P.K., et al. "Protein translocation across planar bilayers by the colicin Ia channel–forming domain: where will it end?" *J Gen Physiol*. Oct. 2000; 116(4):587–98.
Kienker, P.K., et al. "Transmembrane insertion of the colicin Ia hydrophobic hairpin." *J Membr Biol*. May 1, 1997; 157(1):27–37.
Sturme, M.H.J., et al. "Cell to cell communication by autoinducing peptides in gram–positive bacteria." *Antonie Van Leeuwenhoek*. Aug. 2002; 81(1–4):233–43.

* cited by examiner

*Primary Examiner*—Robert A. Wax
(74) *Attorney, Agent, or Firm*—Lahive & Cockfield, LLP

(57) ABSTRACT

Engineered antibiotic peptides and the preparation thereof are provided. The engineered antibiotic peptides, designated pheromonicins, are prepared by linking different bacteriocins or their functional domains with bacterial pheromones. Also provided are methods for treating bacterial infections by use of the antibiotic peptides.

15 Claims, 2 Drawing Sheets a.

b.

70 kDa pheromonicin-SA (634 amino acids)

c.

d.

SEQUENCE LISTING

```
<160> NUMBER OF SEQ ID NOS: 6

<210> SEQ ID NO 1
<211> LENGTH: 8
<212> TYPE: PRT
<213> ORGANISM: Staphylococcus aureus

<400> SEQUENCE: 1

Tyr Ser Thr Cys Asp Phe Ile Met
1               5

<210> SEQ ID NO 2
<211> LENGTH: 7
<212> TYPE: PRT
<213> ORGANISM: Enterococcus fecaelis

<400> SEQUENCE: 2

Leu Val Thr Leu Val Phe Val
1               5

<210> SEQ ID NO 3
<211> LENGTH: 17
<212> TYPE: PRT
<213> ORGANISM: Streptococcus pneumoniae

<400> SEQUENCE: 3

Glu Met Arg Leu Ser Lys Phe Phe Arg Asp Phe Ile Leu Gln Arg Lys
1               5                   10                  15

Lys

<210> SEQ ID NO 4
<211> LENGTH: 66
<212> TYPE: DNA
<213> ORGANISM: Artificial Sequence
<220> FEATURE:
<223> OTHER INFORMATION: 5' cDNA primer which contains the coding
      sequence for agrD bacterial pheromone

<400> SEQUENCE: 4
gcgaataagt tctggggtat ttattccacc tgtgatttta taatgtaaat aaaatataag    60
acaggc                                                              66

<210> SEQ ID NO 5
<211> LENGTH: 63
<212> TYPE: DNA
<213> ORGANISM: Artificial Sequence
<220> FEATURE:
<223> OTHER INFORMATION: 5' cDNA primer which contains the coding
      sequence for CSF bacterial pheromone

<400> SEQUENCE: 5
gcgaataagt tctggggtat tctggttacc cttgtgttcg tgtaaataaa atataagaca    60
```

-continued

```
ggc                                                             63

<210> SEQ ID NO 6
<211> LENGTH: 93
<212> TYPE: DNA
<213> ORGANISM: Artificial Sequence
<220> FEATURE:
<223> OTHER INFORMATION: 5' cDNA primer which contains the coding
      sequence for cCF10 bacterial pheromone

<400> SEQUENCE: 6
gcgaataagt tctggggtat tgaaatgcgt ctgtccaaat ttttccgcga cttcattctg    60
cagcgtaaga aataaataaa atataagaca ggc                                93
```

US 6,942,993 B2

ENGINEERED ANTIBIOTIC PEPTIDES AND THE PREPARATION THEREOF

RELATED APPLICATIONS

Benefit of priority under 35 U.S.C. §119(a) is claimed to Chinese application Serial No. CN 01128836.1, filed on Sep. 11, 2001, entitled "ENGINEERED ANTIBIOTIC PEPTIDES AND THE PREPARATION THEREOF" is claimed. The subject matter of this application is incorporated by reference in its entirety.

FIELD OF INVENTION

The invention relates to engineered antibiotic peptides and the preparation thereof. The engineered antibiotic peptides, designated herein pheromonicins, are prepared by linking different bacteriocins or their functional domains with bacterial pheromones. The invention also relates to method for treating bacterial infections by use of the antibiotic peptides.

BACKGROUND

Bacterial infection still is the main menace of human health. Since sulfamide and penicillin, most antibiotics work to inhibit wall synthesis, to disturb synthesis and metabolism of bacterial nucleic acids and proteins against bacteria. However, mutations arise that result in the development of organisms resistant to these antibiotics. Investigations have been carried on to develop new antibiotics to overpass such bacterial resistance. There is a need to develop new antibiotics.

SUMMARY OF THE INVENTION

In one aspect, the invention provides a new type of antibiotic. Unlike current antibiotics, the new antibiotics do not induce traditional bacterial resistance and have enhanced bactericidal ability. The antibiotics of the invention are engineered peptides, comprising a channel-forming colicin or the channel-forming domain thereof fused with pheromone secreted by the target bacterium. The channel-forming colicin is selected from the group consisting of colicin E1, Ia, Ib, A, B, N and the like. In one embodiment of the invention, the channel-forming colicin is colicin Ia, and the pheromone is Staphylococcus aureus agrD pheromone which has an amino acid sequence of YSTCDFIM(SEQ ID NO:1) (GenBank accession number U85097). In another embodiment of the invention the pheromone is Enterococcus fecaelis pheromone cCF10 having a sequence of LVTLVFV(SEQ ID NO:2). In still another embodiment of the invention, the pheromone is Streptococcus pneumoniae pheromone CSP having a sequence of EMRLSKFFRDFILQRKK(SEQ ID NO:3).

In another aspect, the invention provides a process for the preparation of the engineered antibiotic peptides, which comprises inserting the bacterial pheromone gene into the selected position of colicin gene and introducing thus obtained fusion gene into an expression system to prepare the engineered antibiotic peptide of the invention. In one embodiment of the invention, E.coli is used as the expression system.

In still another aspect, the invention provides a method for treating bacterial infections by use of the antibiotic peptides of the invention. Particularly, the antibiotic peptides of the invention can be used to treat infections caused by bacteria such as Staphylococcus aureus, Enterococcus fecaelis, and Streptococcus pneumoniae. The antibiotic peptides of the invention can advantageously be used to treat infections caused by traditional antibiotic-resistant bacteria.

DESCRIPTION OF THE DRAWINGS

FIG. 1A is a plasmid containing the fusion gene of colicin Ia and Staphylococcus aureus (SA) agrD pheromone (having an amino acid sequence of YSTCDFIM). FIG. 1B is the domain sequence of the pheromonicin construct with the agrD pheromone at the C-terminus. FIG. 1C shows that channels formed by pheromonicin produced a voltage-dependent gating similar to that known to be generated by wild-type colicin Ia on artificial lipid bilayers. FIG. 1D. 15% SDS polyacrylamide gel assay of pheromonicin purified by gradient-elution from a CM column. Lane 1, MW markers; lane 2, proteins eluted with 0.2 M NaCl.

FIG. 2 illustrates the measurement of bactericidal activity of pheromonicin against Staphylococcus aureus (SA), in which;

FIG. 2A shows ATCC 29213 cell growth with 1 µg/ml of pheromonicin or penicillin treatment added when turbidity of cell growth ($A_{595}$) reached between 0.1 and 0.2. PEN, medium with 1 µg/ml penicillin G; Ph-SA, medium with 1 µg/ml pheromonicin prepared in Example 1;

FIG. 2B shows the growth of the methecillin-resistant SA strain (MRSA) ATCC BAA-42 with 5 µg/ml of pheromonicin or oxacillin treatment added when turbidity of cell growth ($A_{595}$) reached between 0.1 and 0.2. Ph-SA (short), medium with 5 µg/ml pheromonicin prepared in Example 2; Ph-SA(long), medium with 5 µg/ml pheromonicin prepared in Example 1; Oxacillin, medium with 5 µg/ml Oxacillin.

FIG. 3 illustrates the measurement of bactericidal activity of pheromonicin against Streptococcus pneumoniae (SP) and Enterococcus feceelis (EF), in which;

FIG. 3A shows Streptococcus pneumoniae BQIOC 31201 cell growth with 5 µg/ml of pheromonicin or penicillin treatment added when turbidity of cell growth ($A_{595nm}$) reached between 0.1 and 0.2. PEN, medium with 5 µg/ml penicillin G; Ph-SA, medium with 5 µg/ml pheromonicin against Staphylococcus aureus prepared in Example 1; Ph-SP, medium with 5 µg/ml pheromonicin against Streptococcus pneumoniae prepared in Example 2; COL, medium with 5 µg/ml wild-type colicin Ia;

FIG. 3B shows the growth of Enterococcus fecaelis ATCC 700802 with 5 µg/ml of pheromonicin or vancomycin treatment added when turbidity of cell growth ($A_{595nm}$) reached between 0.1 and 0.2. Ph-SA, medium with 5 µg/ml pheromonicin against Staphylococcus aureus prepared in Example 1; Ph-EF, medium with 5 µg/ml pheromonicin against Enterococcus fecaelis prepared in Example 2.

DETAILED DESCRIPTION

Figure 1:
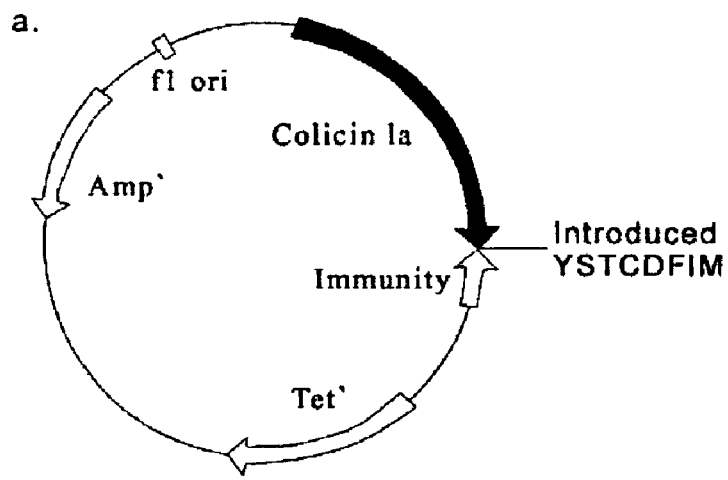
FIG. 1 illustrates the construction and purification of the antibiotic peptide (designated as pheromonicin) of the invention. Specifically.
Figure 1:
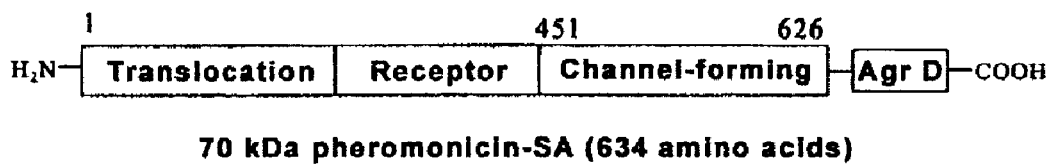
Figure 1:
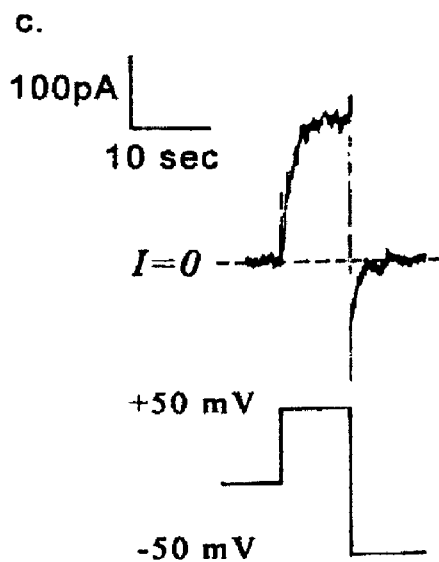
Figure 1:
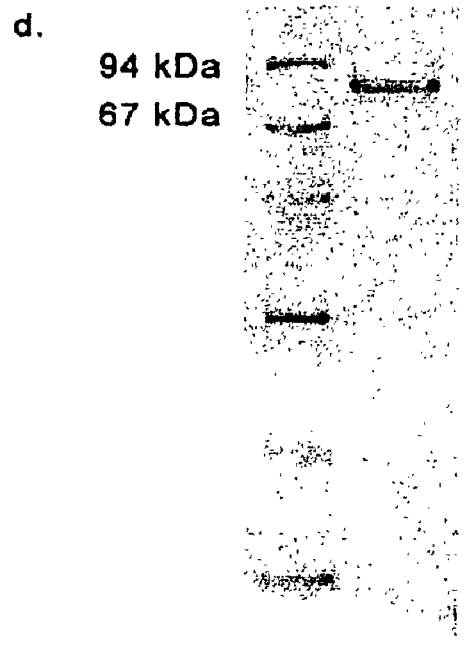
Figure 2:
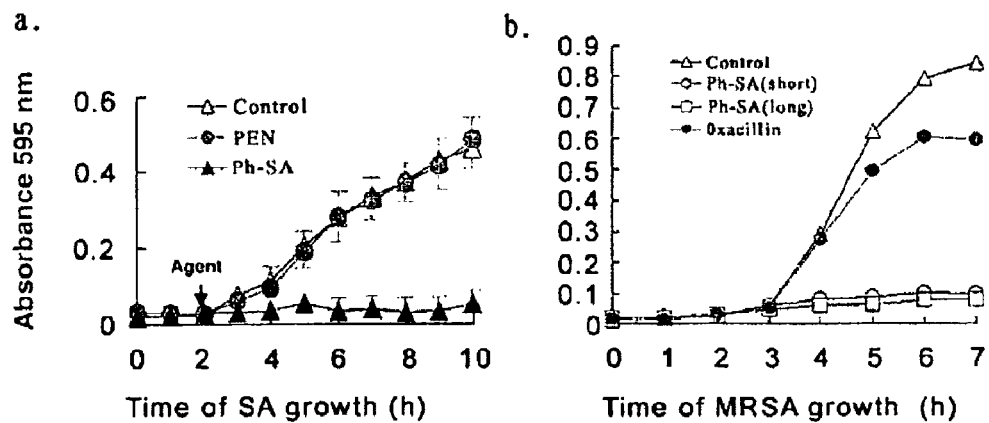
Figure 3:
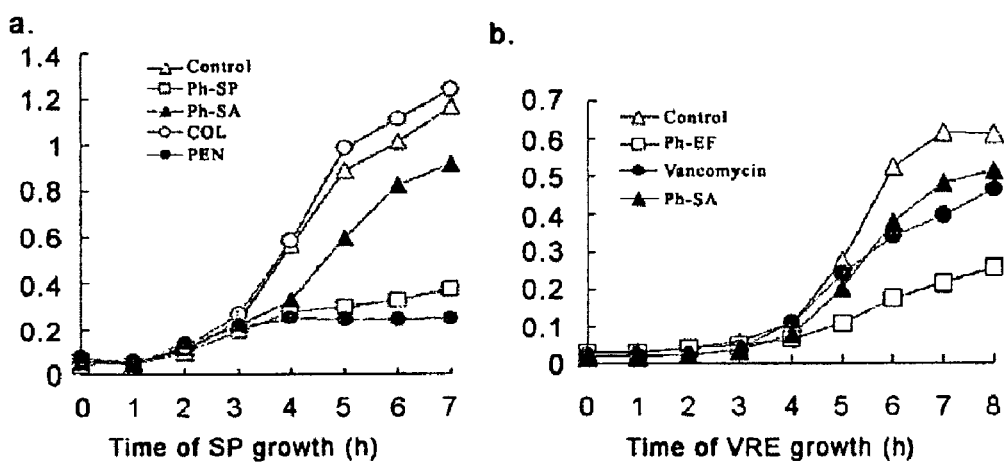
Figure 4:
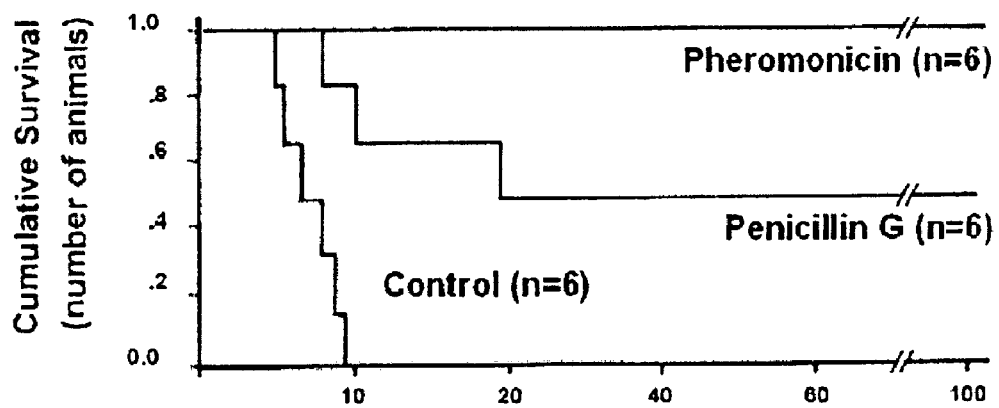
FIG. 4 shows the result of an in vivo test for the bactericidal activity of the antibiotic peptide of the invention.

In nature, many bacteriocins act by forming lethal channels in bacterial cell membranes to kill target bacteria. One typical model is colicin, a toxin protein secreted by Escherichia coli to specifically kill other strains of E.coli and related bacterial species (Jacob et al., Sur Ia biosynthese d'une colicine et son mode d'action, Annals of the Pasteur Institute, 83:295–315(1952)). It was found that the bactericidal effect of colicin occurs by formation of lethal channels in the cell membrane (Schein et al., Colicin K acts by forming voltage-dependent channels in phospholipid bilayer membranes, Nature 276:159–163(1978)). Recently, Qiu and Finkelstein et al. disclosed transmembrane structures of colicin Ia voltage-dependent channel associated with its gating in a phospholipid bilayer membrane (Qiu et al., Major transmembrane movement associated with colicin Ia channel gating, J. Gen. Physiology, 107:313–328(1996)).

During that past twenty years, it was found that bacterial pheromone was an autoinducing signal transduction peptide, normally secreted by bacteria into the medium to interact with a specific membrane receptor of the same strain of cells to regulate the protein expression of bacteria in response to population density. The pheromone of *Staphylococcus aureus*, a typical autoinducing octapeptide, was identified in 1995 (Ji et al., Cell density control of staphylococcal virulence mediated by an octapeptide pheromone, *Proc. Natl. Acad. Sci. U.S.A.* 92:12055–12059(1995)). This octapeptide could stimulate the same *Staphylococcus aureus* strain growth if it was added into the medium during the exponential growth phase of bacteria (Mayville et al., Structure-activity analysis of synthetic autoinducing thiolactone peptides from *Staphylococcus aureus* responsible for virulence (*Proc. Natl. Acad. Sci. U.S.A.* 96:1218–1223(1999)).

As provided herein, these results indicate that channel-forming colicin, an ideal original version, can be used to develop new channel-forming antibiotics. Colicin is an ideal model of a channel-forming antibiotic. Its disadvantage is that it only acts on a very limited number of Gram negative bacteria. It is shown herein that bacterial pheromones can be used to target the channel-forming domain of colicin to contact the cell membrane of target bacteria. Then target bacteria are killed as soon as the colicin channel is formed in their cell membrane.

The engineered antibiotic peptides of the invention comprise a channel-forming colicin or the channel-forming domain thereof fused with a pheromone secreted by the target bacterium. Due to its natural affinity for the membrane receptor of the target bacterium, the pheromone targets the colicin channel-forming domain of the engineered peptide to the cell membrane of the target bacterium. Then the formed channel causes the target bacterium to have leakage and die.

According to the invention, there are two ways to effect linkage of the component peptides of the engineered antibiotic peptide of the invention. The pheromone can be linked either at an N-terminal end or at a C-terminal end of a channel-forming colicin or its channel-forming domain. Thus, there are four forms of the engineered antibiotic peptide, namely, in the N-terminal to C-terminal direction, pheromone fused with channel-forming colicin, channel-forming colicin fused with pheromone, pheromone fused with the channel-forming domain of colicin, and the channel-forming domain of colicin fused with pheromone. In addition, the sequence or structure of pheromone and colicin or its channel-forming domain can be modified either for enhancing bactericidal activity or for decreasing possible side effects. The molecular weight of the engineered peptide may vary within the range of 15,000 to 70,000 Daltons.

In general, any channel-forming colicin can be used in the antibiotic peptide of the invention. For example, the colicin could be selected from the group consisting of colicin E1, Ia, Ib, A, B, N and the like.

It is known that every pathogenic bacterium has its own specific pheromone. Therefore, according to the invention, a highly specific antibiotic peptide can be constructed with the use of a specific pheromone to kill that particular bacterium.

In one embodiment of the invention, the pheromone is *Staphylococcus aureus* agrD pheromone which has an amino acid sequence of YSTCDFIM (GenBank accession number U85097). In addition, pheromones such as the pheromone of *Streptococcus pneumoniae*, CSP, and the pheromone of *Enterococcus faecalis*, cCF10, could also be used. CSP has a sequence of EMRLSKFFRDFILQRKK, and cCF10 has a sequence of LVTLVFV.

According to the invention, the antibiotic peptide can be prepared by expressing in any suitable expression system a fusion gene containing a pheromone gene and a colicin gene. In one embodiment, double-strand oligonucleotide mutagenesis was performed to obtain the fusion gene. It is known to one skilled in the art that other conventional procedures can be taken to obtain the fusion gene.

Compared with traditional antibiotics, the engineered antibiotic peptide of the invention will not induce bacterial resistance that normally occurs with the use of traditional antibiotics. Though not to be bound by any theory, it is believed that bacteria could change their cell wall structure and nucleic acid and protein metabolism through mutation so as to develop resistance against traditional antibiotics. For example, such mutation may produce β-lactamase, decrease intake and change a drug-acting site, causing a change in bacterial cell wall structure and nucleic acid and protein metabolism. However, it would be relatively hard to change lipid bilayer structure of cell membrane via mutation of bacteria. Thus, the bactericidal activity of the antibiotic peptide of the invention could not be deleted by traditional bacterial resistance. The antibiotic peptide of the invention forms a lethal channel in the lipid bilayer of the cell membrane, which is unlikely to be changed by mutation of bacteria.

The above mentioned and further aspects and advantages of the invention will be illustrated in the following non-limiting examples with reference to the above-described drawings.

EXAMPLE 1

This example shows the preparation of an antibiotic peptide containing of *Staphylococcus aureus* (SA) agrD pheromone fused to the C-terminal end of colicin Ia (FIG. 1B). The agrD pheromone has an amino acid sequence of YSTCDFIM (GenBank accession number U85097). Colicin Ia has 626 amino acids in total with an isoleucine residue at the C-terminus (Mankovich, J. A., Hsu, C. H. and Konisky, J., DNA and amino acid sequence analysis of structural and immunity genes of colicin Ia and Ib. J. Bact. 168, 228–236 (1986). Genbank. GB-baiCiaiaimm M13819).

In order to introduce the amino acid sequence of staphylococcal pheromone to follow position I626 of colicin Ia, double-strand oligonucleotide mutagenesis (QuickChange™ kit, Stratagene, catalog #200518) was performed on a Promega pSELECT™-1 plasmid loaded with the colicin Ia gene (generously provided by P. Gosh, UCSF). The 5'-3' oligonucleotide used, containing the desired mutation to introduce the YSTCDFIM peptide at I626 position of colicin Ia was: GCGAATAAGTTCTGGGGTATTTATTC-CACCTGTGATTTTATAATGTAAATAAAATATAA GACAGGC(SEQ ID NO:4). The resultant plasmid (FIG. 1A) was transfected into the TG1 *E. coli* cells to produce the desired antibiotic peptide, which was designated as pheromonicin.

TG1 cells harboring pheromonicin plasmids were grown in FB medium containing 50 μg/ml ampicillin. The harvested cells were resuspended by 60–80 ml borate buffer (pH 9.0, 50 mM borate buffer with 2 mM EDTA and 2 mM DTT) containing 0.5 mM phenylmethylsulfonyl fluoride. The cells were disrupted by sonication and debris was removed by centrifugation for 90 min at 75,000×g. Nucleic acids were removed by the addition of 1/5 volume streptomycin sulfate. The dialyzed extracts were applied to a CM sepharose column (2.5×12 cm) (Pharmacia Biotech, catalog # 17-0719-01). Proteins were then eluted with gradient elution of 0.1, 0.2 and 0.3 M NaCl in borate buffer and collected in 0.5 ml fractions. Total protein concentration of column-eluted solution was about 5 mg/ml. Based on 15% sodium dodecyl sulfate-polyacrylamide gel assay, the pheromonicin eluted by 0.2 M NaCl comprised about 90% of total eluted protein. Thus, the pheromonicin concentration was about more than 4 mg/ml in the stock solution. The molecular weight of the pheromonicin is about 70,000 Daltons FIG. 1D. The pheromonicin thus obtained was used to test its channel-forming activity. FIG. 1C shows that channels formed by the pheromonicin produced a voltage-dependent gating similar to that known to be generated by wild-type colicin Ia on artificial lipid bilayers.

EXAMPLE 2

Basically, as described in Example 1, a pheromonicin containing Staphylococcus aureus agrD pheromone fused to the C-terminal end of the partial channel-forming domain of colicin Ia (Lys524-Ile626 of colicin Ia) was prepared. Said pheromonicin has a molecular weight of about 30,000 Daltons.

Similarly, the CSP pheromone of Streptococcus pneumoniae, EMRLSKFFRDFILQRKK and the cCF10 pheromone of Enterococcus faecalls, LVTLVFV were each introduced following the I626 position of colicin Ia, resulting in specific pheromonicins against Streptococcus pneumoniae and Enterococcus faecalis, respectively. The 5'-3' oligonucleotide used, containing the desired mutation to introduce the LVTLVFV peptide at I626 position of colicin Ia, was: GCGAATAAGTTCTGGGGTATTCTGGTTACCCTTGTGTTCGTG TAAATAAAATATAAGACAGGC(SEQ ID NO:5). The 5'-3' oligonucleotide used, containing the desired mutation to introduce the EMRLSKFFRDFILQRKK peptide at I626 position of colicin Ia was: GCGAATAAGTTCTGGGGTATT GAAATGC GTCTGTCCAAATTTTTCCGCGACTTCATTCT GCAGCGTAAGAAATAAATAAAATATAAGACAGGC(SEQ ID NO:6)

EXAMPLE 3

In Vitro Bactericidal Assays

Bacteria used in the assays were *Staphylococcus aureus* ATCC 29213 (a penicillinase-producing strain), ATCC BAA-42 (a methecillin-resistant strain), *Streptococcus pneumoniae* BQIOC 31201 (Bioproduct Quanrantine Institute of China, originated from National Serum Institute of Denmark) and *Enterococcus fecaelis* ATCC 700802 (a vancomycin-resistant strain).

Cell growth experiments were performed in 100 ml Klett flasks containing 10 ml of BM medium (1% tryptone, 0.5% yeast extract, 0.5% glucose, 1% NaCl, 0.1% $K_2HPO_4$) for staphylococci and reformed BM medium with 2.7 gm MH culture /100 ml for streptococci and Enterococci and monitored turbimetrically with a BioRad 550 microplate reader read at OD 595 nm by every 60 min. Cells were inoculated to an initial cell density of $2.5\times10^5$ CFU/ml and shaken at around 200 rpm on an orbital shaker at 37° C.

FIG. 2 illustrates the result of the in vitro cell growth assay which tested the bactericidal activity of pheromonicin against *Staphylococcus aureus* (SA) Specifically, FIG. 2A shows ATCC 29213 cell growth with 1 μg/ml of pheromonicin (prepared in Example 1) or penicillin treatment added when turbidity of cell growth ($A_{595}$) reached between 0.1 and 0.2. FIG. 2B shows the growth of the methecillin-resistant SA strain (MRSA) ATCC BAA-42 with 5 μg/ml of pheromonicin (prepared in Example 1 and 2 respectively) or oxacillin treatment added when turbidity of cell growth ($A_{595}$) reached between 0.1 and 0.2. In both assays, growth medium with 0.2 M NaCl borate buffer is used as a control.

It can be seen from FIG. 2 that the antibiotic peptides of the invention have superior activity of killing *Staphylococcus aureus.* They can kill the *Staphylococcus aureus* strains which are resistant against penicillin and oxacillin.

FIG. 3 illustrates the result of the in vitro cell growth assay which tested the bactericidal activity of pheromonicins against *Streptococcus pneumoniae* (SP) and *Enterococcus fecaelis* (EF). Specifically, FIG. 3A shows *Streptococcus pneumoniae* BQIOC 31201 cell growth with 5 μg/ml of pheromonicin or penicillin treatment added when turbidity of cell growth ($A_{595}$) reached between 0.1 and 0.2. FIG. 3B shows the growth of *Enterococcus fecaelis* ATCC 700802 with 5 μg/ml of pheromonicin or vancomycin treatment added when turbidity of cell growth ($A_{595}$) reached between 0.1 and 0.2.

It can be seen from FIG. 3 that the antibiotic peptides of the invention are highly specific narrow-spectrum antibiotics. For example, it is shown in FIG. 3A that only pheromonicin containing the pheromone of *Streptococcus pneumoniae* (Ph-SP, prepared in Example 2) could kill *Streptococcus pneumoniae* cells. The pheromonicin containing the pheromone of *Staphylococcus aureus* (Ph-SA, prepared in Example 1) did not affect the cell growth of *Streptococcus pneumoniae.* Similarly, in FIG. 3B, it is shown that only pheromonicin containing the pheromone of *Enterococcus fecaelis* could kill *Enterococcus fecaelis* cells and pheromonicin containing the pheromone of *Staphylococcus aureus* did not affect the cell growth of *Enterococcus feceelis*. It is also significant that the antibiotic peptide of the invention can kill a vancomycin-resistant strain of *Enterococcus fecaelis.* So far no routine antibiotic can kill such strains.

EXAMPLE 4

In Vivo Test

This test is performed to determine whether the antibiotic peptide of the invention could be effective as a targeted antibiotic in vivo.

Eighteen mice (Kungming mice, from experimental animal center of West China University of Medical Sciences, Chengdu, Sichuan, China) were divided into three groups, and each mouse in all three groups was injected with a lethal dose of *Staphylococcus aureus* ATCC 29213 cells intraperitoneally. After 1 hr, the mice of Group 1 were injected with 2.5 mg of penicillin G, the mice of Group 2 were injected with 2 mg of pheromonicin prepared in Example 1, and the mice of Group 3 were injected with saline as a control. The injections were repeated every 6 hours for a total of 4 doses in those surviving animals. FIG. 4 shows that all mice in the control group (n=6) died in less than 10 hrs. In contrast, 50% of the penicillin treated group (n=6) died in 20 hrs. However, all mice in the pheromonicin treated group (n=6) survived over 100 hrs. Fifty percent of the penicillin group also survived over 100 hours. Kaplan-Meier analysis showed that the results of the pheromonicin-treated vs. control groups were statistically significant with P=0.0005.

EXAMPLE 5

An antibiotic peptide containing the Staphylococcal pheromone agrD fused to the N-terminal end of the colicin Ia channel-forming domain was prepared as described in Example 1. The molecular weight of the resultant peptide was measured as about 30,000 Daltons. Experiments showed that the peptide presented certain bactericidal effects against *Staphylococcus aureus* (data not shown).

EXAMPLE 6

An antibiotic peptide containing the Staphylococcal pheromone agrD fused to the N-terminal end of wild-type colicin Ia were prepared as described in Example 1. The molecular weight of the resultant peptide was measured as about 70,000 Daltons. Experiments showed that the peptide presented certain bactericidal effects against *Staphylococcus aureus* (data not shown).

---

I claim:

1. An engineered antibiotic peptide, comprising a fusion protein of a pheromone of a pathogenic bacterium fused to a channel-forming colicin or its channel-forming domain.

2. The antibiotic peptide of claim 1 selected from the group consisting of the pheromone fused with the channel-forming colicin, the channel-forming colicin fused with the pheromone, the pheromone fused with the channel-forming domain of the colicin, and the channel-forming domain of the colicin fused with the pheromone, where the components are recited in the N-terminal to C-terminal direction.

3. The engineered antibiotic peptide of claim 1, wherein the structure of said engineered antibiotic peptide is such that the pheromone is linked to the C-terminus of the colicin or its channel-forming domain.

4. The engineered antibiotic peptide of claim 1, wherein the structure of said engineered antibiotic peptide is such that the pheromone is linked to the N-terminus of the colicin or its channel-forming domain.

5. The engineered antibiotic peptide of claim 1, wherein the channel-forming colicin is selected from the group consisting of colicin E1. Ia, Ib. A, B and N.

6. The engineered antibiotic peptide of claim 1, wherein the channel-forming colicin is colicin Ia.

7. The engineered antibiotic peptide of claim 1, wherein the pheromone is a pheromone of a pathogenic bacterium selected from among *Staphylococcus aureus, Streptococcus pneumoniae* and *Entorococcus fecaelis*.

8. The engineered antibiotic peptide as claimed in claim 6, wherein the pheromone is selected from the group consisting of *Staphylococcus aureus* pheromone agrD, *Streptococcus pneumoniae* pheromone CSP, and *Entorococcus fecaelis* pheromone cCF10.

9. The engineered antibiotic peptide of claim 1, wherein *Staphylococcus aureus* pheromone agrD is fused to the C-terminal of colicin Ia, as shown in FIG. 1.

10. The engineered antibiotic peptide of claim 1. wherein *Staphylococcus aureus* pheromone agrD is fused to the C-terminus of the colicin Ia channel-forming domain.

11. The engineered antibiotic peptide of claim 1, wherein *Streptococcus pneumoniae* pheromone CSP is fused to the C-terminus of colicin Ia.

12. The engineered antibiotic peptide of claim 1, wherein *Enterococcus fecaells* pheromone cCF10 is fused to the C-terminus of colicin Ia.

13. A process for preparing an engineered antibiotic peptide, comprising the steps of:
  a) inserting a bacterial pheromone gene into a selected position of a colicin gene to produce a fusion gene;
  b) introducing the fusion gene into an expression system; and
  C) expressing and harvesting the engineered antibiotic peptide from the expression system.

14. A method for treating bacterial infection, comprising administering an effective amount of an antibiotic peptide of claim 1.

15. The method of claim 14, wherein the bacterial infection is selected from a group consisting of *Staphylococcus aureus* infection, *Streptococcus pneumoniae* infection, and *Enterococcus fecaelis* infection.

* * * * *